(12) United States Patent
Bevers et al.

(10) Patent No.: US 11,499,142 B2
(45) Date of Patent: Nov. 15, 2022

(54) ENZYME COMPOSITION

(71) Applicant: DSM IP Assets B.V., Heerlen (NL)

(72) Inventors: Loes Elizabeth Bevers, Echt (NL); Maaike Appeldoorn, Echt (NL); Margot Elisabeth Francoise Schooneveld-Bergmans, Echt (NL); Herman Jan Pel, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 82 days.

(21) Appl. No.: 16/463,074

(22) PCT Filed: Nov. 23, 2017

(86) PCT No.: PCT/EP2017/080158
§ 371 (c)(1),
(2) Date: May 22, 2019

(87) PCT Pub. No.: WO2018/096019
PCT Pub. Date: May 31, 2018

(65) Prior Publication Data
US 2019/0284594 A1    Sep. 19, 2019

(30) Foreign Application Priority Data

Nov. 24, 2016 (EP) .................................... 16200553

(51) Int. Cl.
| | |
|---|---|
| *C12N 9/00* | (2006.01) |
| *C12N 9/42* | (2006.01) |
| *C12N 9/02* | (2006.01) |
| *C12N 9/26* | (2006.01) |
| *C12P 19/00* | (2006.01) |
| *C12N 9/24* | (2006.01) |
| *C12P 7/10* | (2006.01) |
| *C12P 19/02* | (2006.01) |
| *C12P 19/14* | (2006.01) |
| *C12N 9/18* | (2006.01) |

(52) U.S. Cl.
CPC ............. *C12N 9/00* (2013.01); *C12N 9/0071* (2013.01); *C12N 9/18* (2013.01); *C12N 9/24* (2013.01); *C12N 9/2402* (2013.01); *C12N 9/244* (2013.01); *C12N 9/2437* (2013.01); *C12N 9/2445* (2013.01); *C12N 9/2448* (2013.01); *C12N 9/2477* (2013.01); *C12P 7/10* (2013.01); *C12P 19/02* (2013.01); *C12P 19/14* (2013.01); *C12Y 302/01004* (2013.01); *C12Y 302/0115* (2013.01); *C12Y 302/01021* (2013.01); *C12Y 302/01037* (2013.01); *C12Y 302/01136* (2013.01); *Y02E 50/10* (2013.01)

(58) Field of Classification Search
CPC .. C12N 9/0083; C12N 9/2437; C12N 9/2477; C12P 7/10; C12P 9/00
See application file for complete search history.

(56) References Cited

U.S. PATENT DOCUMENTS

| | | | |
|---|---|---|---|
| 2015/0299749 A1* | 10/2015 | Noordam ................ | C12P 19/02 |
| | | | 435/99 |
| 2016/0201102 A1* | 7/2016 | Zhu .......................... | C12P 7/10 |
| | | | 435/68.1 |

FOREIGN PATENT DOCUMENTS

| | | | |
|---|---|---|---|
| WO | 20120044835 A1 | 4/2012 | |
| WO | 20140092832 A2 | 6/2014 | |
| WO | WO-2015017869 A1 * | 2/2015 | ............... C12P 7/10 |

OTHER PUBLICATIONS

X4YXV3. UniProtKB Database. Jun. 11, 2014.*
International Search Report for PCT/EP2017/080158, dated Nov. 1, 2018.
J.S. Van Dyk et al: "A review of lignocellulose bioconversion using enzymatic hydrolysis and synergistic cooperation between enzymes-Factors affecting enzymes, conversion and synergy", Biotechnology Advances, vol. 30, No. 6, Nov. 1, 2012 (Nov. 1, 2012), pp. 1458-1480.
Poidevin L et al: "Comparative analyses of Podospora anserina secretomes reveal a large array of lignocellulose-active enzymes", Applied Microbiology and Biotechnology 2014, vol. 98, No. 17, 2014, pp. 7457-7469.
Dimarogona et al., "Lignin boosts the cellulase performance of a GH-61 enzyme from Sporotrichum thermophile", Bioresource, Technology, vol. 110, 2012, pp. 480-487.

* cited by examiner

*Primary Examiner* — Yong D Pak
(74) *Attorney, Agent, or Firm* — McBee Moore & Vanik IP, LLC; Susan McBee; Chester Moore

(57) ABSTRACT

The application relates to an enzyme composition, a process for the preparation thereof and the use of the enzyme composition in enzymatic hydrolysis.

15 Claims, No Drawings

ENZYME COMPOSITION

CROSS-REFERENCE TO RELATED APPLICATIONS

This application is the National Stage entry of International Application No. PCT/EP2017/080158, filed 23 Nov. 2017, which claims priority to European Patent Application No. 16200553.2, filed 24 Nov. 2017.

BACKGROUND

Field

The disclosure relates to an enzyme composition, a process for the preparation thereof and the use of the enzyme composition in enzymatic hydrolysis.

DESCRIPTION OF RELATED ART

Lignocellulosic material is primarily composed of cellulose, hemicellulose and lignin and provides an attractive platform for generating alternative energy sources to fossil fuels. The material is available in large amounts and can be converted into valuable products e.g. sugars or biofuel, such as bioethanol.

Producing fermentation products from lignocellulosic material is known in the art and generally includes the steps of pretreatment, hydrolysis, fermentation, and optionally recovery of the fermentation products.

During the hydrolysis, which may comprise the steps of liquefaction, pre-saccharification and/or saccharification, cellulose present in the lignocellulosic material is partly (typically 30 to 95%, dependable on enzyme activity and hydrolysis conditions) converted into reducing sugars by cellulolytic enzymes. The hydrolysis typically takes place during a process lasting 6 to 168 hours under elevated temperatures of 45 to 50° C. and non-sterile conditions.

Commonly, the sugars are converted into valuable fermentation products such as ethanol by microorganisms like yeast. The fermentation takes place in a separate, preferably anaerobic, process step, either in the same or in a different vessel. The temperature during fermentation is adjusted to 30 to 33° C. to accommodate growth and ethanol production by microorganisms, commonly yeasts. During the fermentation process, the remaining cellulosic material is converted into reducing sugars by the enzymes already present from the hydrolysis step, while microbial biomass and ethanol are produced. The fermentation is finished once the cellulosic material is converted into fermentable sugars and all fermentable sugars are converted into ethanol, carbon dioxide and microbial biomass. This may take up to 6 days. In general, the overall process time of hydrolysis and fermentation may amount up to 13 days.

The cost of enzyme production is a major cost factor in the overall production process of fermentation products from lignocellulosic material. Therefore, several approaches have been taken to decrease the costs of enzymes and enzyme compositions, for example, increasing the amount of enzymes produced by a production microorganism, modulation and construction of new and improved enzymes by mutagenesis techniques and exploration of genetic diversity.

All these approaches have not increased the enzymatic activity sufficiently to overcome the high cost of enzyme production in the overall production process of fermentation products from lignocellulosic material. One drawback of these approaches has been the focus on a single enzyme at a time, neglecting the synergies possible with other cellulolytic enzymes.

Several attempts have been made to develop enzyme compositions to maximize the enzymatic hydrolysis of lignocellulosic material. For example, WO 2011/000949 describes Talaromyces mutant strains that produce specific enzyme compositions that can be used in enzymatic hydrolysis of lignocellulosic material.

However, these attempts have not succeeded in developing enzyme compositions with sufficiently improved performance for the hydrolysis of lignocellulosic biomass.

Thus, in spite of much research effort, there remains a need for improved enzyme compositions that reduce overall production costs in the process involving hydrolysis and fermentation of lignocellulosic material.

SUMMARY

An object of the disclosure is to provide an improved enzyme composition, process of making the enzyme composition and use of the enzyme composition in a process for the preparation of a sugar product and/or a fermentation product from lignocellulosic material.

DETAILED DESCRIPTION

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

In the context of the disclosure, "improved" and/or "increased" is used to indicate that an enzyme composition comprising an endoglucanase and a lytic polysaccharide monooxygenase, wherein the endoglucanase is present at a fraction relative to the endoglucanase (EG) and the lytic polysaccharide monooxygenase (LPMO) as defined by $R_{EG}$ and wherein the lytic polysaccharide monooxygenase is present at a fraction relative to the lytic polysaccharide monooxygenase and the endoglucanase as defined by $R_{LPMO}$, wherein $R_{EG}$ is from 0.05 to 0.34 and $R_{LPMO}$ is from 0.66 to 0.95 shows a higher glucan and xylan conversion under the same process or the same process conditions compared to an enzyme composition comprising an endoglucanase and an lytic polysaccharide monooxygenase, wherein the endoglucanase is present at a fraction relative to the endoglucanase and the lytic polysaccharide monooxygenase as defined by $R_{EG}$ and wherein the lytic polysaccharide monooxygenase is present at a fraction relative to the lytic polysaccharide monooxygenase and the endoglucanase as defined by $R_{LPMO}$, wherein $R_{EG}$ is below 0.05 or above 0.34 and $R_{LPMO}$ is below 0.66 or above 0.95.

The present disclosure relates to an enzyme composition comprising an endoglucanase and a lytic polysaccharide monooxygenase, wherein the endoglucanase is present at a fraction relative to the endoglucanase and the lytic polysaccharide monooxygenase as defined by $R_{EG}$ and wherein the lytic polysaccharide monooxygenase is present at a fraction relative to the lytic polysaccharide monooxygenase and the endoglucanase as defined by $R_{LPMO}$, wherein $R_{EG}$ is from 0.05 to 0.34 and $R_{LPMO}$ is from 0.66 to 0.95. Preferably, $R_{EG}$ is from 0.06 to 0.30 and $R_{LPMO}$ is from 0.70 to 0.94. More preferably, $R_{EG}$ is from 0.08 to 0.28 and $R_{LPMO}$ is from 0.72 to 0.92.

The ratio endoglucanase ($R_{EG}$), which is defined as the total weight of endoglucanases in the enzyme composition divided by the total weight of endoglucanases and the total weight of lytic polysaccharide monooxygenases in the enzyme composition, can be calculated by the formula: $R_{EG}$=total EG/(total EG+total LPMO). The ratio lytic polysaccharide monooxygenases ($R_{LPMO}$), which is defined as the total weight of lytic polysaccharide monooxygenases in the enzyme composition divided by the total weight of lytic polysaccharide monooxygenases and the total weight of endoglucanases in the enzyme composition can be calculated by the formula: $R_{LPMO}$=total LPMO/(total EG+total LPMO).

As described herein the enzyme composition of the present disclosure comprises an endoglucanase and a lytic polysaccharide monooxygenase. It is to be understood that "an endoglucanase" means "at least one endoglucanase" and that "a lytic polysaccharide monooxygenase" means "at least one lytic polysaccharide monooxygenase". The enzyme composition of the present disclosure may thus comprise more than one endoglucanase and/or more than one lytic polysaccharide monooxygenase. In case, there are several endoglucanases and/or several lytic polysaccharide monooxygenases, $R_{EG}$ relates to the weight of all endoglucanases in the enzyme composition divided by the total weight of endoglucanases and lytic polysaccharide monooxygenases in the enzyme composition and $R_{LPMO}$ relates to the weight of all lytic polysaccharide monooxygenases in the enzyme composition divided by the total weight of endoglucanases and lytic polysaccharide monooxygenases in the enzyme composition.

As used herein, lytic polysaccharide monooxygenases are enzymes that have recently been classified by CAZy in family AA9 (Auxiliary Activity Family 9) or family AA10 (Auxiliary Activity Family 10). Ergo, there exist AA9 lytic polysaccharide monooxygenases and AA10 lytic polysaccharide monooxygenases. Lytic polysaccharide monooxygenases are able to open a crystalline glucan structure and enhance the action of cellulases on lignocellulose substrates. They are enzymes having cellulolytic enhancing activity. Lytic polysaccharide monooxygenases may also affect cellooligosaccharides. According to the latest literature, (see Isaksen et al., Journal of Biological Chemistry, vol. 289, no. 5, p. 2632-2642), proteins named GH61 (glycoside hydrolase family 61 or sometimes referred to EGIV) are lytic polysaccharide monooxygenases. GH61 was originally classified as endoglucanase based on measurement of very weak endo-1,4-β-d-glucanase activity in one family member, but have recently been reclassified by CAZy in family AA9. CBM33 (family 33 carbohydrate-binding module) is also a lytic polysaccharide monooxygenase (see Isaksen et al, Journal of Biological Chemistry, vol. 289, no. 5, pp. 2632-2642). CAZy has recently reclassified CBM33 in the AA10 family.

In an embodiment the lytic polysaccharide monooxygenase comprises an AA9 lytic polysaccharide monooxygenase. This means that at least one of the lytic polysaccharide monooxygenases in the enzyme composition is an AA9 lytic polysaccharide monooxygenase. In an embodiment all lytic polysaccharide monooxygenases in the enzyme composition are AA9 lytic polysaccharide monooxygenase.

In an embodiment the enzyme composition comprises a lytic polysaccharide monooxygenase from *Thermoascus*, such as *Thermoascus aurantiacus*, such as the one described in WO 2005/074656 as SEQ ID NO:2 and SEQ ID NO:1 in WO2014/130812 and in WO 2010/065830; or from *Thielavia*, such as *Thielavia terrestris*, such as the one described in WO 2005/074647 as SEQ ID NO: 8 or SEQ ID NO:4 in WO2014/130812 and in WO 2008/148131, and WO 2011/035027; or from *Aspergillus*, such as *Aspergillus fumigatus*, such as the one described in WO 2010/138754 as SEQ ID NO:2 or SEQ ID NO: 3 in WO2014/130812; or from *Penicillium*, such as *Penicillium emersonii*, such as the one disclosed as SEQ ID NO:2 in WO 2011/041397 or SEQ ID NO:2 in WO2014/130812. Other suitable lytic polysaccharide monooxygenases include, but are not limited to, *Trichoderma reesei* (see WO 2007/089290), *Myceliophthora thermophila* (see WO 2009/085935, WO 2009/085859, WO 2009/085864, WO 2009/085868), *Penicillium pinophilum* (see WO 2011/005867), *Thermoascus* sp. (see WO 2011/039319), and *Thermoascus crustaceous* (see WO 2011/041504). Other cellulolytic enzymes that may be comprised in the enzyme composition are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593, to name just a few. In a preferred embodiment, the lytic polysaccharide monooxygenase is from *Rasamsonia*, e.g. *Rasamsonia emersonii* (see WO 2012/000892).

In an embodiment the enzyme composition comprises lytic polysaccharide monooxygenase in an amount of 10% to 30% (w/w) of the total amount of protein in the enzyme composition.

As used herein, endoglucanases are enzymes which are capable of catalyzing the endohydrolysis of 1,4-β-D-glucosidic linkages in cellulose, lichenin or cereal β-D-glucans. They belong to EC 3.2.1.4 and may also be capable of hydrolyzing 1,4-linkages in β-D-glucans also containing 1,3-linkages. Endoglucanases may also be referred to as cellulases, avicelases, β-1,4-endoglucan hydrolases, β-1,4-glucanases, carboxymethyl cellulases, celludextrinases, endo-1,4-β-D-glucanases, endo-1,4-β-D-glucanohydrolases or endo-1,4-β-glucanases.

In an embodiment the endoglucanase comprises a GH5 endoglucanase and/or a GH7 endoglucanase. This means that at least one of the endoglucanases in the enzyme composition is a GH5 endoglucanase or a GH7 endoglucanase. In case there are more endoglucanases in the enzyme composition, these endoglucanases can be GH5 endoglucanases, GH7 endoglucanases or a combination of GH5 endoglucanases and GH7 endoglucanases. In a preferred embodiment the endoglucanase comprises a GH5 endoglucanase.

In an embodiment the enzyme composition comprises an endoglucanase from *Trichoderma*, such as *Trichoderma reesei*; from *Humicola*, such as a strain of *Humicola insolens*; from *Aspergillus*, such as *Aspergillus aculeatus* or *Aspergillus kawachii*; from *Erwinia*, such as *Erwinia carotovara*; from *Fusarium*, such as *Fusarium oxysporum*; from *Thielavia*, such as *Thielavia terrestris*; from *Humicola*, such as *Humicola grisea* var. *thermoidea* or *Humicola insolens*; from *Melanocarpus*, such as *Melanocarpus albomyces*;

from *Neurospora*, such as *Neurospora crassa*; from *Myceliophthora*, such as *Myceliophthora thermophila*; from *Cladorrhinum*, such as *Cladorrhinum foecundissimum*; and/or from *Chrysosporium*, such as a strain of *Chrysosporium lucknowense*. In a preferred embodiment the endoglucanase is from *Rasamsonia*, such as a strain of *Rasamsonia emersonii* (see WO 01/70998). In an embodiment even a bacterial endoglucanase can be used including, but are not limited to, *Acidothermus cellulolyticus* endoglucanase (see WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (see WO 05/093050); and *Thermobifida fusca* endoglucanase V (see WO 05/093050).

In an embodiment the enzyme composition comprises endoglucanase in an amount of 3% to 5% (w/w) of the total amount of protein in the enzyme composition. In an embodiment the enzyme composition comprises endoglucanase in an amount of 3% to 4.5% (w/w) of the total amount of protein in the enzyme composition.

In an embodiment the enzyme composition of the present disclosure further comprises a hemicellulase. In an embodiment, the enzyme composition further comprises a hemicellulase, wherein the hemicellulase is present at a fraction relative to the hemicellulase and the lytic polysaccharide monooxygenase as defined by $R_{HC}$, wherein $R_{HC}$ is from 0.15 to 0.65. Preferably, $R_{HC}$ is from 0.20 to 0.60. More preferably, $R_{HC}$ is from 0.22 to 0.55.

As described herein the enzyme composition of the present disclosure comprises a hemicellulase. It is to be understood that "a hemicellulase" means "at least one hemicellulase". The enzyme composition of the present disclosure may thus comprise more than one hemicellulase.

In an embodiment the hemicellulase comprises a beta-xylosidase and/or an endoxylanase.

The ratio hemicellulase ($R_{HC}$), which is defined as the total weight of beta-xylosidases and endoxylanases in the enzyme composition divided by the total weight of beta-xylosidases, endoxylanases and lytic polysaccharide monooxygenases in the enzyme composition, can be calculated by the formula: $R_{HC}$=(total BX+total EX)/(total BX+total EX+total LPMO).

In case, there are several beta-xylosidases and/or several endoxylanases, $R_{HC}$ relates to the weight of all beta-xylosidases and all endoxylanases in the enzyme composition divided by the total weight of all beta-xylosidases, all endoxylanases and all lytic polysaccharide monooxygenases in the enzyme composition.

As used herein, beta-xylosidases (EC 3.2.1.37) are polypeptides which are capable of catalysing the hydrolysis of 1,4-β-D-xylans, to remove successive D-xylose residues from the non-reducing termini. Beta-xylosidases may also hydrolyze xylobiose. Beta-xylosidase may also be referred to as xylan 1,4-β-xylosidase, 1,4-β-D-xylan xylohydrolase, exo-1,4-β-xylosidase or xylobiase.

In an embodiment the beta-xylosidase comprises a GH3 beta-xylosidase. This means that at least one of the beta-xylosidases in the enzyme composition is a GH3 beta-xylosidase. In an embodiment all beta-xylosidases in the enzyme composition are GH3 beta-xylosidases.

In an embodiment the enzyme composition comprises a beta-xylosidase from *Neurospora crassa, Aspergillus fumigatus* or *Trichoderma reesei*. In a preferred embodiment the enzyme composition comprises a beta-xylosidase from *Rasamsonia*, such as *Rasamsonia emersonii* (see WO 2014/118360).

As used herein, an endoxylanase (EC 3.2.1.8) is any polypeptide which is capable of catalysing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyze 1,4 xylosidic linkages in glucuronoarabinoxylans.

In an embodiment the endoxylanase comprises a GH10 xylanase. This means that at least one of the endoxylanases in the enzyme composition is a GH10 xylanase. In an embodiment all endoxylanases in the enzyme composition are GH10 xylanases.

In an embodiment the enzyme composition comprises an endoxylanase from *Aspergillus aculeatus* (see WO 94/21785), *Aspergillus fumigatus* (see WO 2006/078256), *Penicillium pinophilum* (see WO 2011/041405), *Penicillium sp.* (see WO 2010/126772), *Thielavia terrestris* NRRL 8126 (see WO 2009/079210), *Talaromyces leycettanus, Thermobifida fusca*, or *Trichophaea saccata* GH10 (see WO 2011/057083). In a preferred embodiment the enzyme composition comprises an endoxylanase from *Rasamsonia*, such as *Rasamsonia emersonii* (see WO 02/24926).

In an embodiment the enzyme composition further comprises a beta-glucosidase (BG), a cellobiohydrolase I (CBHI) and a cellobiohydrolase II (CBHII).

As used herein, a beta-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

In an embodiment the enzyme composition comprises a beta-glucosidase from *Aspergillus*, such as *Aspergillus oryzae*, such as the one disclosed in WO 02/095014 or the fusion protein having beta-glucosidase activity disclosed in WO 2008/057637, or *Aspergillus fumigatus*, such as the one disclosed as SEQ ID NO:2 in WO 2005/047499 or SEQ ID NO:5 in WO 2014/130812 or an *Aspergillus fumigatus* beta-glucosidase variant, such as one disclosed in WO 2012/044915, such as one with the following substitutions: F100D, S283G, N456E, F512Y (using SEQ ID NO: 5 in WO 2014/130812 for numbering), or *Aspergillus aculeatus, Aspergillus niger* or *Aspergillus kawachi*. In another embodiment the beta-glucosidase is derived from *Penicillium*, such as *Penicillium brasilianum* disclosed as SEQ ID NO:2 in WO 2007/019442, or from *Trichoderma*, such as *Trichoderma reesei*, such as ones described in U.S. Pat. Nos. 6,022,725, 6,982,159, 7,045,332, 7,005,289, US 2006/0258554 US 2004/0102619. In an embodiment even a bacterial beta-glucosidase can be used. In another embodiment the beta-glucosidase is derived from *Thielavia terrestris* (WO 2011/035029) or *Trichophaea saccata* (WO 2007/019442). In a preferred embodiment the enzyme composition comprises a beta-glucosidase from *Rasamsonia*, such as *Rasamsonia emersonii* (see WO 2012/000886).

As used herein, a cellobiohydrolase (EC 3.2.1.91) is any polypeptide which is capable of catalyzing the hydrolysis of 1,4-β-D-glucosidic linkages in cellulose or cellotetraose, releasing cellobiose from the ends of the chains. This enzyme may also be referred to as cellulase 1,4-βcellobiosidase, 1,4-β-cellobiohydrolase, 1,4-β-D-glucan cellobiohydrolase, avicelase, exo-1,4-β-D-glucanase, exo-cellobiohydrolase or exoglucanase.

In an embodiment the enzyme composition comprises a cellobiohydrolase I from *Aspergillus*, such as *Aspergillus fumigatus*, such as the Cel7A CBH I disclosed in SEQ ID NO:6 in WO 2011/057140 or SEQ ID NO:6 in WO 2014/130812; from *Trichoderma*, such as *Trichoderma reesei*; from *Chaetomium*, such as *Chaetomium thermophilum*; from *Talaromyces*, such as *Talaromyces leycettanus* or from *Penicillium*, such as *Penicillium emersonii*. In a preferred embodiment the enzyme composition comprises a cellobiohydrolase I from *Rasamsonia*, such as *Rasamsonia emersonii* (see WO 2010/122141).

In an embodiment the enzyme composition comprises a cellobiohydrolase II from *Aspergillus*, such as *Aspergillus fumigatus*, such as the one in SEQ ID NO:7 in WO 2014/130812 or from *Trichoderma*, such as *Trichoderma reesei*, or from *Talaromyces*, such as *Talaromyces leycettanus*, or from *Thielavia*, such as *Thielavia terrestris*, such as cellobiohydrolase II CEL6A from *Thielavia terrestris*. In a preferred embodiment the enzyme composition comprises a cellobiohydrolase II from *Rasamsonia*, such as *Rasamsonia emersonii* (see WO 2011/098580).

An enzyme composition comprises preferably at least two activities, although typically a composition will comprise more than two activities, for example, three, four, five, six, seven, eight, nine or even more activities. An enzyme composition may comprise more than one enzyme activity per activity class. For example, an enzyme composition may comprise two endoglucanase activities, for example, endo-1,3(1,4)-β glucanase activity and endo-β-1,4-glucanase activity. An enzyme composition may comprise one type of cellulase activity and/or hemicellulase activity and/or pectinase activity.

In an embodiment the enzyme composition comprises at least two cellulases. As used herein, a cellulase is any polypeptide which is capable of degrading or modifying cellulose. The at least two cellulases may contain the same or different activities. The enzyme composition may also comprises at least one enzyme other than a cellulase, e.g. a hemicellulase or a pectinase. As used herein, a hemicellulase is any polypeptide which is capable of degrading or modifying hemicellulose. As used herein, a pectinase is any polypeptide which is capable of degrading or modifying pectin. The at least one other enzyme may have an auxiliary enzyme activity, i.e. an additional activity which, either directly or indirectly leads to lignocellulose degradation. Examples of such auxiliary activities are mentioned herein.

In an embodiment the enzyme composition as described herein comprises one, two, three, four classes or more of cellulase, for example one, two, three or four or all of a lytic polysaccharide monooxygenase (LPMO), an endoglucanase (EG), one or two cellobiohydrolases (CBH) and a beta-glucosidase (BG).

In an embodiment the enzyme composition as described herein comprises a lytic polysaccharide monooxygenase, an endoglucanase, a cellobiohydrolase I, a cellobiohydrolase II, a beta-glucosidase, a beta-xylosidase and an endoxylanase.

In an embodiment the enzyme composition also comprises one or more of the below mentioned enzymes.

As used herein, a β-(1,3)(1,4)-glucanase (EC 3.2.1.73) is any polypeptide which is capable of catalysing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucane when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase. Substrates include laminarin, lichenin and cereal beta-D-glucans.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase. Examples of arabinofuranosidases that may be comprised in the enzyme composition include, but are not limited to, arabinofuranosidases from *Aspergillus niger, Humicola insolens* DSM 1800 (see WO 2006/114094 and WO 2009/073383) and *M. giganteus* (see WO 2006/114094).

As used herein, an α-D-glucuronidase (EC 3.2.1.139) is any polypeptide which is capable of catalysing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. An alternative is EC 3.2.1.131: xylan alpha-1,2-glucuronosidase, which catalyses the hydrolysis of alpha-1,2-(4-O-methyl)glucuronosyl links. Examples of alpha-glucuronidases that may be comprised in the enzyme composition include, but are not limited to, alpha-glucuronidases from *Aspergillus clavatus, Aspergillus fumigatus, Aspergillus niger, Aspergillus terreus, Humicola insolens* (see WO 2010/014706), *Penicillium aurantiogriseum* (see WO 2009/068565) and *Trichoderma reesei*.

As used herein, an acetyl xylan esterase (EC 3.1.1.72) is any polypeptide which is capable of catalysing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin. Examples of acetylxylan esterases that may be comprised in the enzyme composition include, but are not limited to, acetylxylan esterases from *Aspergillus aculeatus* (see WO 2010/108918), *Chaetomium globosum, Chaetomium gracile, Humicola insolens* DSM 1800 (see WO 2009/073709), *Hypocrea jecorina* (see WO 2005/001036), *Myceliophtera thermophila* (see WO 2010/014880), *Neurospora crassa, Phaeosphaeria nodorum* and *Thielavia terrestris* NRRL 8126 (see WO 2009/042846). In a preferred embodiment the enzyme composition comprises an acetyl xylan esterase from *Rasamsonia*, such as *Rasamsonia emersonii* (see WO 2010/000888)

As used herein, a feruloyl esterase (EC 3.1.1.73) is any polypeptide which is capable of catalysing a reaction of the form: feruloyl-saccharide+$H_2O$=ferulate+saccharide. The saccharide may be, for example, an oligosaccharide or a polysaccharide. It may typically catalyse the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin. Examples of feruloyl esterases (ferulic acid esterases) that may be comprised in the enzyme composition include, but are not limited to, feruloyl esterases form *Humicola insolens* DSM 1800 (see WO 2009/076122), *Neosartorya fischeri, Neurospora crassa, Penicillium aurantiogriseum* (see WO 2009/127729), and *Thielavia terrestris* (see WO 2010/053838 and WO 2010/065448).

As used herein, a coumaroyl esterase (EC 3.1.1.73) is any polypeptide which is capable of catalysing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

As used herein, an α-galactosidase (EC 3.2.1.22) is any polypeptide which is capable of catalysing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

As used herein, a β-galactosidase (EC 3.2.1.23) is any polypeptide which is capable of catalysing the hydrolysis of terminal non-reducing β-D-galactose residues in β-D-galactosides. Such a polypeptide may also be capable of hydrolyzing α-L-arabinosides. This enzyme may also be referred to as exo-(1→4)-β-D-galactanase or lactase.

As used herein, a β-mannanase (EC 3.2.1.78) is any polypeptide which is capable of catalysing the random hydrolysis of 1,4-β-D-mannosidic linkages in mannans, galactomannans and glucomannans. This enzyme may also be referred to as mannan endo-1,4-β-mannosidase or endo-1,4-mannanase.

As used herein, a β-mannosidase (EC 3.2.1.25) is any polypeptide which is capable of catalysing the hydrolysis of terminal, non-reducing β-D-mannose residues in β-D-mannosides. This enzyme may also be referred to as mannanase or mannase.

As used herein, an endo-polygalacturonase (EC 3.2.1.15) is any polypeptide which is capable of catalysing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

As used herein, a pectin methyl esterase (EC 3.1.1.11) is any enzyme which is capable of catalysing the reaction: pectin+n H$_2$O=n methanol+pectate. The enzyme may also been known as pectinesterase, pectin demethoxylase, pectin methoxylase, pectin methylesterase, pectase, pectinoesterase or pectin pectylhydrolase.

As used herein, an endo-galactanase (EC 3.2.1.89) is any enzyme capable of catalysing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

As used herein, a pectin acetyl esterase is defined herein as any enzyme which has an acetyl esterase activity which catalyses the deacetylation of the acetyl groups at the hydroxyl groups of GalUA residues of pectin.

As used herein, an endo-pectin lyase (EC 4.2.2.10) is any enzyme capable of catalysing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

As used herein, a pectate lyase (EC 4.2.2.2) is any enzyme capable of catalysing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

As used herein, an alpha rhamnosidase (EC 3.2.1.40) is any polypeptide which is capable of catalysing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

As used herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

As used herein, exo-galacturonase (EC 3.2.1.67) is any polypeptide capable of catalysing: (1,4-α-D-galacturonide)$_n$+H$_2$O=(1,4-α-D-galacturonide)$_{n-1}$+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1.4-α-D-galacturonide) galacturonohydrolase.

As used herein, exopolygalacturonate lyase (EC 4.2.2.9) is any polypeptide capable of catalysing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

As used herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

As used herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

As used herein, rhamnogalacturonan acetyl esterase is any polypeptide which catalyzes the deacetylation of the backbone of alternating rhamnose and galacturonic acid residues in rhamnogalacturonan.

As used herein, rhamnogalacturonan galacturonohydrolase is any polypeptide which is capable of hydrolyzing galacturonic acid from the non-reducing end of strictly alternating rhamnogalacturonan structures in an exo-fashion.

As used herein, xylogalacturonase is any polypeptide which acts on xylogalacturonan by cleaving the β-xylose substituted galacturonic acid backbone in an endo-manner. This enzyme may also be known as xylogalacturonan hydrolase.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, endo-arabinanase (EC 3.2.1.99) is any polypeptide which is capable of catalysing endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

"Protease" includes enzymes that hydrolyze peptide bonds (peptidases), as well as enzymes that hydrolyze bonds between peptides and other moieties, such as sugars (glycopeptidases). Many proteases are characterized under EC 3.4 and are suitable for use in the processes as described herein. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalysing a transferase reaction, but which can also catalyze a hydrolysis reaction, for example of cellulose and/or cellulose degradation products. An example of a hexosyltransferase which may be used is a β-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucuronoside, for example β-glucuronoside to yield an alcohol. Many glucuronidases have been characterized and may be suitable for use, for example β-glucuronidase (EC 3.2.1.31), hyaluronoglucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. As described herein, an expansin-like protein or swollenin-like protein may comprise one or both of such domains and/or may disrupt the structure of cell walls (such as disrupting cellulose structure), optionally without producing detectable amounts of reducing sugars.

A cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multi-functional integrating subunits which may organize cellulolytic subunits into a multienzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein may comprise one or both of such domains.

A catalase; the term "catalase" means a hydrogen-peroxide: hydrogen-peroxide oxidoreductase (EC 1.11.1.6 or EC 1.11.1.21) that catalyzes the conversion of two hydrogen peroxides to oxygen and two waters. Catalase activity can be determined by monitoring the degradation of hydrogen peroxide at 240 nm based on the following reaction: $2H_2O \rightarrow 2H_2O+O_2$. The reaction is conducted in 50 mM phosphate pH 7.0 at 25° C. with 10.3 mM substrate ($H_2O_2$) and approximately 100 units of enzyme per ml. Absorbance is monitored spectrophotometrically within 16-24 seconds, which should correspond to an absorbance reduction from 0.45 to 0.4. One catalase activity unit can be expressed as one micromole of $H_2O_2$ degraded per minute at pH 7.0 and 25° C.

The term "amylase" as used herein means enzymes that hydrolyze alpha-1,4-glucosidic linkages in starch, both in amylose and amylopectin, such as alpha-amylase (EC 3.2.1.1), beta-amylase (EC 3.2.1.2), glucan 1,4-alpha-glucosidase (EC 3.2.1.3), glucan 1,4-alpha-maltotetraohydrolase (EC 3.2.1.60), glucan 1,4-alpha-maltohexaosidase (EC 3.2.1.98), glucan 1,4-alpha-maltotriohydrolase (EC 3.2.1.116) and glucan 1,4-alpha-maltohydrolase (EC 3.2.1.133), and enzymes that hydrolyze alpha-1,6-glucosidic linkages, being the branch-points in amylopectin, such as pullulanase (EC 3.2.1.41) and limit dextinase (EC 3.2.1.142).

An enzyme composition may be composed of a member of each of the classes of enzymes mentioned above, several members of one enzyme class, or any combination of these enzyme classes. Different enzymes in an enzyme composition as described herein may be obtained from different sources.

In the uses and processes described herein, the components of the compositions described above may be provided concomitantly (i.e. as a single composition per se) or separately or sequentially.

In an embodiment the enzymes in the enzyme composition are derived from a fungus, preferably a filamentous fungus or the enzymes comprise a fungal enzyme, preferably a filamentous fungal enzyme. In a preferred embodiment the fungus is *Rasamsonia*, with *Rasamsonia emersonii* being most preferred. In an embodiment a core set of (ligno) cellulose degrading enzymes (i.e. cellulases and/or a hemicellulases and/or a pectinases) may be derived from *Rasamsonia emersonii*. If needed, the set of enzymes can be supplemented with additional enzyme activities from other sources. Such additional activities may be derived from classical sources and/or produced by genetically modified organisms. Thus, the enzyme composition may comprise a cellulase and/or a hemicellulase and/or a pectinase from a source other than *Rasamsonia*. In an embodiment they may be used together with one or more *Rasamsonia* enzymes or they may be used without additional *Rasamsonia* enzymes being present.

"Filamentous fungi" include all filamentous forms of the subdivision *Eumycota* and *Oomycota* (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Agaricus, Aspergillus, Aureobasidium, Beauvaria, Cephalosporium, Ceriporiopsis, Chaetomium paecilomyces, Chrysosporium, Claviceps, Cochiobolus, Coprinus, Cryptococcus, Cyathus, Emericella, Endothia, Endothia mucor, Filibasidium, Fusarium, Geosmithia, Gilocladium, Humicola, Magnaporthe, Mucor, Myceliophthora, Myrothecium, Neocallimastix, Neurospora, Paecilomyces, Penicillium, Piromyces, Panerochaete, Pleurotus, Podospora, Pyricularia, Rasamsonia, Rhizomucor, Rhizopus, Scylatidium, Schizophyllum, Stagonospora, Talaromyces, Thermoascus, Thermomyces, Thielavia, Tolypocladium, Trametes, Trichoderma* and *Trichophyton*.

Several strains of filamentous fungi are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL). Examples of such strains include *Aspergillus niger* CBS 513.88, *Aspergillus oryzae* ATCC 20423, IFO 4177, ATCC 1011, ATCC 9576, ATCC14488-14491, ATCC 11601, ATCC12892, *Penicillium chrysogenum* CBS 455.95, *Penicillium citrinum* ATCC 38065, *Penicillium chrysogenum* P2, *Talaromyces emersonii* CBS 393.64, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* C1, Garg 27K, VKM F-3500-D, ATCC44006 and derivatives thereof.

The enzymes (for example in the form of a whole fermentation broth) may be prepared by fermentation of a suitable substrate with a suitable microorganism, e.g. a filamentous fungus, wherein the enzymes are produced by the microorganism. The microorganism may be altered to improve or to make the enzymes. For example, the microorganism may be mutated by classical strain improvement procedures or by recombinant DNA techniques. Therefore, the microorganisms mentioned herein can be used as such to produce the enzymes or may be altered to increase the production or to produce altered enzymes, which might include heterologous enzymes, e.g. cellulases and/or hemicellulases and/or pectinases, thus enzymes that are not originally produced by that microorganism. Preferably, a fungus, more preferably a filamentous fungus, is used to produce the enzymes. Advantageously, a thermophilic or thermotolerant microorganism is used. Optionally, a substrate is used that induces the expression of the enzymes by the enzyme producing microorganism.

In an embodiment the enzyme composition comprises a "thermostable" enzyme. A "thermostable" enzyme as used herein means that the enzyme has a temperature optimum of 50° C. or higher, 60° C. or higher, 70° C. or higher, 75° C. or higher, 80° C. or higher, 85° C. or higher. They may for example be isolated from thermophilic microorganisms or may be designed by the skilled person and artificially synthesized. In one embodiment the polynucleotides may be isolated or obtained from thermophilic or thermotolerant filamentous fungi or isolated from non-thermophilic or non-thermotolerant fungi, but are found to be thermostable.

By "thermophilic fungus" is meant a fungus that grows at a temperature of 50° C. or higher. By "themotolerant" fungus is meant a fungus that grows at a temperature of 45° C. or higher, having a maximum near 50° C.

Suitable thermophilic or thermotolerant fungal cells may be a *Humicola, Rhizomucor, Myceliophthora, Rasamsonia, Talaromyces, Thermomyces, Thermoascus* or *Thielavia* cell, preferably a *Rasamsonia* cell. Preferred thermophilic or thermotolerant fungi are *Humicola grisea* var. thermoidea, *Humicola lanuginosa, Myceliophthora thermophila, Papulaspora thermophilia, Rasamsonia byssochlamydoides, Rasamsonia emersonii, Rasamsonia argillacea, Rasamsonia eburnean, Rasamsonia brevistipitata, Rasamsonia cylindrospora, Rhizomucor pusillus, Rhizomucor miehei, Talaromyces bacillisporus, Talaromyces leycettanus, Talaromyces thermophilus, Thermomyces lenuginosus, Thermoascus crustaceus, Thermoascus thermophilus Thermoascus aurantiacus* and *Thielavia terrestris*.

Thermophilic fungi are not restricted to a specific taxonomic order and occur all over the fungal tree of life. Examples are *Rhizomucor* in the Mucorales, *Myceliophthora* in Sordariales and *Talaromyces, Thermomyces* and *Thermoascus* in the Eurotiales (see Mouchacca, 1997). The majority of *Talaromyces* species are mesophiles, but exceptions are species within sections *Emersonii* and *Thermophila*.Section *Emersonii* includes *Talaromyces emersonii, Talaromyces byssochlamydoides, Talaromyces bacillisporus* and *Talaromyces leycettanus*, all of which grow well at 40° C. *Talaromyces bacillisporus* is thermotolerant, *Talaromyces leycettanus* is thermotolerant to thermophilic, and *Talaromyces emersonii* and *Talaromyces byssochlamydoides* are truly thermophilic (see Stolk and Samson, 1972). The sole member of *Talaromyces* section *Thermophila, Talaromyces thermophilus*, grows rapidly at 50° C. (see Stolk and Samson, 1972). The current classification of these thermophilic *Talaromyces* species is mainly based on phenotypic and physiological characters, such as their ability to grow above 40° C., ascospore color, the structure of ascornatal covering and the formation of a certain type of anamorph. Stolk and Samson (1972) stated that the members of the section *Emersonii* have anamorphs of either *Paecilomyces* (*Talaromyces byssochlamydoides* and *Talaromyces leycettanus*) or *Penicillium cylindrosporum* series (*Talaromyces emersonii* and *Talaromyces bacillisporus*). Later, Pitt (1979) transferred the species belonging to the *Penicillium cylindrosporum* series to the genus *Geosmithia*, based on various characters such as the formation of conidia from terminal pores instead of on collula (necks), a character of *Penicillium* and *Paecilomyces*. Within the genus *Geosmithia*, only *Geosmithia argillacea* is thermotolerant, and Stolk et al. (1969) and Evans (1971) proposed a connection with members of *Talaromyces* sect. *Emersonii*. The phylogenetic relationship of the themophilic *Talaromyces* species within *Talaromyces* and the *Trichocomaceae* is unknown (see J. Houbraken, Antonie van Leeuwenhoek 2012 February; 101 (2): 403-21).

*Rasamsonia* is a new genus comprising thermotolerant and thermophilic *Talaromyces* and *Geosmithia* species (J. Houbraken et al., vida supra). Based on phenotypic, physiological and molecular data, Houbraken et al. proposed to transfer the species *Talaromyces emersonii, Talaromyces byssochlamydoides, Talaromyces eburneus, Geosmithia argillacea* and *Geosmithia cylindrospora* to *Rasamsonia* gen. nov.

Preferred thermophilic fungi are *Rasamsonia byssochlamydoides, Rasamsonia emersonii, Thermomyces lenuginosus, Talaromyces thermophilus, Thermoascus crustaceus, Thermoascus thermophilus* and *Thermoascus aurantiacus*, with *Rasamsonia emersonii* being most preferred. *Talaromyces emersonii, Penicillium geosmithia emersonii* and *Rasamsonia emersonii* are used interchangeably herein.

In an embodiment the enzyme composition is a whole fermentation broth. In an embodiment the enzyme composition is a whole fermentation broth of a fungus, preferably a filamentous fungus, preferably of the genus *Rasamsonia*. The whole fermentation broth can be prepared from fermentation of non-recombinant and/or recombinant filamentous fungi. In an embodiment the filamentous fungus is a recombinant filamentous fungus comprising one or more genes which can be homologous or heterologous to the filamentous fungus. In an embodiment, the filamentous fungus is a recombinant filamentous fungus comprising one or more genes which can be homologous or heterologous to the filamentous fungus, wherein the one or more genes encode enzymes that can degrade a cellulosic substrate. The whole fermentation broth may comprise any of the polypeptides described herein or any combination thereof.

Preferably, the enzyme composition is a whole fermentation broth, wherein cells are killed, i.e. nonviable. In an embodiment the whole fermentation broth comprises polypeptides, organic acid(s), killed cells and/or cell debris, and culture medium.

Generally, the filamentous fungi are cultivated in a cell culture medium suitable for production of enzymes capable of hydrolyzing a cellulosic substrate. The cultivation takes place in a suitable nutrient medium comprising carbon and nitrogen sources and inorganic salts, using procedures known in the art. Suitable culture media, temperature ranges and other conditions suitable for growth and cellulase and/or hemicellulase and/or pectinase production are known in the art. The whole fermentation broth can be prepared by growing the filamentous fungi to stationary phase and maintaining the filamentous fungi under limiting carbon conditions for a period of time sufficient to express the one or more cellulases and/or hemicellulases and/or pectinases. Once enzymes, such as cellulases and/or hemicellulases and/or pectinases, are secreted by the filamentous fungi into the fermentation medium, the whole fermentation broth can be used. The whole fermentation broth may comprise filamentous fungi. In an embodiment, the whole fermentation broth comprises the unfractionated contents of the fermentation materials derived at the end of the fermentation. Typically, the whole fermentation broth comprises the spent culture medium and cell debris present after the filamentous fungi are grown to saturation, incubated under carbon-limiting conditions to allow protein synthesis (particularly, expression of cellulases and/or hemicellulases and/or pectinases). In some embodiments, the whole fermentation broth comprises the spent cell culture medium, extracellular enzymes and filamentous fungi. The filamentous fungal cells present in whole fermentation broth can be killed using methods known in the art to produce a cell-killed whole fermentation broth. For instance, addition of organic acid leads to killing of the cells. If needed, the cells may also be lysed and/or permeabilized. In an embodiment, the whole fermentation broth is a cell-killed whole fermentation broth, wherein the whole fermentation broth containing the filamentous fungal cells are killed. In other words, the whole fermentation broth comprises more nonviable cells than viable cells, preferably only nonviable cells. In some embodiments, the cells are killed by lysing the filamentous fungi by chemical and/or pH treatment to generate the cell-killed whole broth of a fermentation of the filamentous fungi. In some embodiments, the cells are killed by lysing the filamentous fungi by chemical and/or pH treatment and adjusting the pH of the cell-killed fermentation mix to a suitable pH. In an embodiment, the whole fermentation broth is mixed with an organic acid.

The term "whole fermentation broth" as used herein refers to a preparation produced by cellular fermentation that undergoes no or minimal recovery and/or purification. For example, whole fermentation broths are produced when microbial cultures are grown to saturation, incubated under carbon-limiting conditions to allow protein synthesis (e.g., expression of enzymes by host cells) and secretion into cell culture medium. Typically, the whole fermentation broth is unfractionated and comprises spent cell culture medium, extracellular enzymes, and microbial, preferably nonviable, cells.

In an embodiment the whole fermentation broth can be fractionated and the one or more of the fractionated contents can be used. For instance, the killed cells and/or cell debris can be removed from a whole fermentation broth to provide an enzyme composition that is free of these components.

The whole fermentation broth may further comprise a preservative and/or anti-microbial agent. Such preservatives and/or agents are known in the art. In an embodiment the orgnic acid used for killing the cells can also have the function of preservative and/or anti-microbial agent.

The whole fermentation broth as described herein is typically a liquid, but may contain insoluble components, such as killed cells, cell debris, culture media components, and/or insoluble enzyme(s). In some embodiments, insoluble components may be removed to provide a clarified whole fermentation broth.

In an embodiment, the whole fermentation broth may be supplemented with one or more enzyme activities that are not expressed endogenously, or expressed at relatively low level by the filamentous fungi, to improve the degradation of the cellulosic substrate, for example, to fermentable sugars such as glucose or xylose. The supplemental enzyme(s) can be added as a supplement to the whole fermentation broth, i.e. they are spiked to the whole fermentation broth. The additional enzymes may be supplemented in the form of a whole fermentation broth, or may be supplemented as purified, or minimally recovered and/or purified, enzymes.

In an embodiment, the whole fermentation broth may be supplemented with at least another whole fermentation broth. The other whole fermentation broth may be derived from the same type of fungus or from another type of fungus, e.g. a first whole fermentation broth may be derived from *Rasamsonia*, while a second whole fermentation broth may be derived from *Rasamsonia* or *Aspergillus*.

In an embodiment, the whole fermentation broth is a whole fermentation broth of a fermentation of a recombinant filamentous fungi overexpressing one or more enzymes to improve the degradation of the cellulosic substrate. Alternatively, the whole fermentation broth is a mixture of a whole fermentation broth of a fermentation of a non-recombinant filamentous fungus and a whole fermentation broth of a recombinant filamentous fungus overexpressing one or more enzymes to improve the degradation of the cellulosic substrate. In an embodiment, the whole fermentation broth is a whole fermentation broth of a fermentation of a filamentous fungi overexpressing beta-glucosidase. Alternatively, the whole fermentation broth is a mixture of a whole fermentation broth of a fermentation of a non-recombinant filamentous fungus and a whole fermentation broth of a fermentation of a recombinant filamentous fungi overexpressing a beta-glucosidase.

In an embodiment the enzyme composition as described herein has a pH of 2.0 to 5.5. Preferably, the enzyme composition has a pH of 2.5 to 5.0. More preferably, the enzyme composition has a pH of 3.0 to 4.5. Ergo, the enzymes in the enzyme composition are able to work at low pH.

In an embodiment the container(s) used in the process for the preparation of an enzyme composition as described herein have a volume of at least 1 $m^3$. Preferably, the containers have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 $m^3$, at least 40 $m^3$, at least 45 $m^3$, at least 50 $m^3$, at least 60 $m^3$, at least 70 $m^3$, at least 75 $m^3$, at least 80 $m^3$, at least 90 $m^3$. In general, the container(s) will be smaller than 300 $m^3$.

In the process for the preparation of an enzyme composition as described herein, a population of microbial cells, e.g. filamentous fungal cells, is cultured under suitable conditions for growth, in a liquid or solid medium. In an embodiment the microbial cells are cultured in a fed-batch culture, a batch culture, a continuous culture or any combination thereof. Preferably, the filamentous fungus are cultured in a fed-batch culture. A person skilled in the art is well aware of the various modes of culturing and its conditions. In an embodiment the culturing is conducted under aerobic conditions. A person skilled in the art is well aware of fermentor designs for aerobic cultivation such as for instance stirred tanks and bubble columns.

The present disclosure relates to a process for the preparation of a sugar from lignocellulosic material comprising the steps of (a) hydrolysing the lignocellulosic material with an enzyme composition as described herein to obtain the sugar, and (b) optionally, recovering the sugar.

The present disclosure also relates to a process for producing a fermentation product from a lignocellulosic material, which process comprises the steps of (a) hydrolysing the lignocellulosic material with an enzyme composition as described herein to obtain a sugar, (b) fermenting the obtained sugar by contacting the obtained sugar with a fermenting microorganism to produce the fermentation product, and (c) optionally, recovering the fermentation product.

After enzymatic hydrolysis, the hydrolysed lignocellulosic material may be subjected to at least one solid/liquid separation. The methods and conditions of solid/liquid separation will depend on the type of lignocellulosic material used and are well within the scope of the skilled artisan. Examples include, but are not limited to, centrifugation, cyclonic separation, filtration, decantation, sieving and sedimentation. In a preferred embodiment the solid/liquid separation is performed by centrifugation or sedimentation. During solid/liquid separation, means and/or aids for improving the separation may be used.

In an embodiment the lignocellulosic material is subjected to a pretreatment step before the enzymatic hydrolysis. In an embodiment the lignocellulosic material is subjected to a washing step before the enzymatic hydrolysis. In an embodiment the lignocellulosic material is subjected to at least one solid/liquid separation before the enzymatic hydrolysis. So, before subjecting the lignocellulosic material to enzymatic hydrolysis, it can be subjected to at least one solid/liquid separation. The solid/liquid separation may be done before and/or after the pretreatment step. Suitable methods and conditions for a solid/liquid separation have been described above.

In an embodiment the enzymatically hydrolysed lignocellulosic material is subjected to a solid/liquid separation step followed by a detoxification step and/or a concentration step.

In the processes as described herein lignocellulosic material may be added to the one or more containers. In an embodiment the enzyme composition is already present in the one or more containers before the lignocellulosic material is added. In another embodiment the enzyme composition may be added to the one or more containers. In an embodiment the lignocellulosic material is already present in the one or more containers before the enzyme composition is added. In an embodiment both the lignocellulosic material and the enzyme composition are added simultaneously to the one or more containers. The enzyme composition present in the one or more containers may be an aqueous composition.

In an embodiment the enzymatic hydrolysis comprises at least a liquefaction step wherein the lignocellulosic material is hydrolysed in at least a first container, and a saccharification step wherein the liquefied lignocellulosic material is hydrolysed in the at least first container and/or in at least a second container. Saccharification can be done in the same container as the liquefaction (i.e. the at least first container), it can also be done in a separate container (i.e. the at least second container). So, in the enzymatic hydrolysis liquefaction and saccharification may be combined. Alternatively, the liquefaction and saccharification may be separate steps. Liquefaction and saccharification may be performed at different temperatures, but may also be performed at a single temperature. In an embodiment the temperature of the liquefaction is higher than the temperature of the saccharification. Liquefaction is preferably carried out at a temperature of 60-85° C. and saccharification is preferably carried out at a temperature of 50-65° C.

The enzymatic hydrolysis can be performed in one or more containers, but can also be performed in one or more tubes or any other continuous system. This also holds true when the enzymatic hydrolysis comprises a liquefaction step and a saccharification step. The liquefaction step can be performed in one or more containers, but can also be performed in one or more tubes or any other continuous system and/or the saccharification step can be performed in one or more containers, but can also be performed in one or more tubes or any other continuous system. Examples of containers to be used include, but are not limited to, fed-batch stirred containers, batch stirred containers, continuous flow stirred containers with ultrafiltration, and continuous plug-flow column reactors. Stirring can be done by one or more impellers, pumps and/or static mixers.

The enzymes used in the enzymatic hydrolysis may be added before and/or during the enzymatic hydrolysis. As indicated above, when the lignocellulosic material is subjected to a solid/liquid separation before enzymatic hydrolysis, the enzymes used in the enzymatic hydrolysis may be added before the solid/liquid separation. Alternatively, they may also be added after solid/liquid separation or before and after solid/liquid separation. The enzymes may also be added during the enzymatic hydrolysis. In case the enzymatic hydrolysis comprises a liquefaction step and saccharification step, additional enzymes may be added during and/or after the liquefaction step. The additional enzymes may be added before and/or during the saccharification step. Additional enzymes may also be added after the saccharification step.

In an embodiment the total enzymatic hydrolysis time is 10 hours or more, 12 hours or more, 14 hours or more, 16 hours or more, 18 hours or more, 20 hours or more, 30 hours or more, 40 hours or more, 50 hours or more, 60 hours or more, 70 hours or more, 80 hours or more, 90 hours or more, 100 hours or more, 110 hours or more, 120 hours or more, 130 hours or more, 140 hours or more, 150 hours or more, 160 hours or more, 170 hours or more, 180 hours or more, 190 hours or more, 200 hours or more.

In an embodiment, the total enzymatic hydrolysis time is 10 to 300 hours, 16 to 275 hours, preferably 20 to 250 hours, more preferably 30 to 200 hours, most preferably 40 to 150 hours.

The viscosity of the lignocellulosic material in the one or more containers used for the enzymatic hydrolysis is kept between 10 and 4000 cP, between 10 and 2000 cP, preferably between 10 and 1000 cP.

In case the process comprises an enzymatic hydrolysis comprising a liquefaction step and a saccharification step, the viscosity of the lignocellulosic material in the liquefaction step is kept between 10 and 4000 cP, between 10 and 2000 cP, preferably between 10 and 1000 cP and/or the viscosity of the lignocellulosic material in the saccharification step is kept between 10 and 1000 cP, between 10 and 900 cP, preferably between 10 and 800 cP.

The viscosity can be determined with a Brookfield DV III Rheometer at the temperature used for the hydrolysis.

In an embodiment oxygen is added during the enzymatic hydrolysis. In an embodiment oxygen is added during at least a part of the enzymatic hydrolysis. Oxygen can be added continuously or discontinuously during the enzymatic hydrolysis. In an embodiment oxygen is added one or more times during the enzymatic hydrolysis. In an embodiment oxygen may be added before the enzymatic hydrolysis, during the addition of lignocellulosic material to a container used for enzymatic hydrolysis, during the addition of enzyme to a container used for enzymatic hydrolysis, during a part of the enzymatic hydrolysis, during the whole enzymatic hydrolysis or any combination thereof. Oxygen is added to the one or more containers used in the enzymatic hydrolysis.

Oxygen can be added in several forms. For example, oxygen can be added as oxygen gas, oxygen-enriched gas, such as oxygen-enriched air, or air. Oxygen may also be added by means of in situ oxygen generation. For example, oxygen may be generated by electrolysis, oxygen may be produced enzymatically, e.g. by the addition of peroxide, or oxygen may be produced chemically, e.g. by an oxygen generating system such as $KHSO_5$. For example, oxygen is produced from peroxide by catalase. The peroxide can be added in the form of dissolved peroxide or generated by an enzymatic or chemical reaction. In case catalase is used as enzyme to produce oxygen, catalase present in the enzyme composition for the hydrolysis can be used or catalase can be added for this purpose.

Examples how to add oxygen include, but are not limited to, addition of oxygen by means of sparging, electrolysis, chemical addition of oxygen, filling the one or more containers used in the enzymatic hydrolysis from the top (plunging the hydrolysate into the tank and consequently introducing oxygen into the hydrolysate) and addition of oxygen to the headspace of said one or more containers. When oxygen is added to the headspace of the container(s), sufficient oxygen necessary for the hydrolysis reaction may be supplied. In general, the amount of oxygen added to the container(s) can be controlled and/or varied. Restriction of the oxygen supplied is possible by adding only oxygen during part of the hydrolysis time in said container(s). Another option is adding oxygen at a low concentration, for example by using a mixture of air and recycled air (air leaving the container) or by "diluting" air with an inert gas. Increasing the amount of oxygen added can be achieved by addition of oxygen during longer periods of the hydrolysis time, by adding the oxygen at a higher concentration or by adding more air. Another way to control the oxygen concentration is to add an oxygen consumer and/or an oxygen generator. Oxygen can be introduced, for example blown, into the liquid hydrolysis container contents of lignocellulosic material. It can also be blown into the headspace of the container.

In an embodiment oxygen is added to the one or more containers used in the enzymatic hydrolysis before and/or during and/or after the addition of the lignocellulosic material to said one or more containers. The oxygen may be introduced together with the lignocellulosic material that enters the hydrolysis container(s). The oxygen may be introduced into the material stream that will enter the container(s) or with part of the container(s) contents that passes an external loop of the container(s).

In an embodiment the container(s) used in the enzymatic hydrolysis and/or the fermentation have a volume of at least 1 $m^3$. Preferably, the containers have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 $m^3$, at least 40 $m^3$, at least 45 $m^3$, at least 50 $m^3$, at least 60 $m^3$, at least 70 $m^3$, at least 75 $m^3$, at least 80 $m^3$, at least 90 $m^3$, at least 100 $m^3$, at least 200 $m^3$, at least 300 $m^3$, at least 400 $m^3$, at least 500 $m^3$, at least 600 $m^3$, at least 700 $m^3$, at least 800 $m^3$, at least 900 $m^3$, at least 1000 $m^3$, at least 1500 $m^3$, at least 2000 $m^3$, at least 2500 $m^3$. In general, the container(s) will be smaller than 3000 $m^3$ or 5000 $m^3$. In case several containers are used in the enzymatic hydrolysis, they may have the same volume, but also may have a different volume. In case the enzymatic hydrolysis comprises a separate liquefaction step and saccharification step the container(s) used for the liquefaction step and the container(s) used for the saccharification step may have the same volume, but also may have a different volume.

The enzymatic hydrolysis is preferably done at a temperature of 40° C. or more, preferably 45° C. or more. In an embodiment the enzymatic hydrolysis is done at a temperature of 40-90° C., preferably 45-90° C. In this step, thermostable cellulolytic enzymes are preferred.

In a common process for converting lignocellulosic material into fermentation products, process steps are preferably done under septic conditions to lower the operational costs. Contamination and growth of contaminating microorganisms can therefore occur and result in undesirable side effects, such as lactic acid, formic acid and acetic acid production, yield losses of fermentation product on substrate, production of toxins and extracellular polysaccharides. These effects may affect production costs significantly. A high process temperature and/or a short process time limits the risk on contamination during hydrolysis and fermentation. Thermostable enzymes, like those of *Rasamsonia*, are capable of hydrolysing lignocellulosic material at temperatures of higher than 60° C. At these temperatures, the risk that a contaminating microorganism will cause undesired side effects is little to almost zero.

During the fermentation step, in which for example ethanol is produced, temperatures are typically between 30 to 38° C. and are preferably not raised because of production losses. By applying short fermentation process times, the risks and effects of contamination and/or growth of contaminants are reduced as much as possible. With stable enzymes, like those of *Rasamsonia*, a short fermentation time can be applied and thus risks of contamination and/or growth of contaminants are reduced as much as possible. The cost reduction achieved with applying thermostable cellulolytic enzymes of Rasamsonia in this way, results in a lower risk of process failures due to contamination.

The first step after thermal pretreatment is to cool the pretreated material to temperatures wherein the enzymes have an optimal activity. On large scale, this is typically done by adding (cooled) water, which, besides decreasing the temperature, reduces the dry matter content. By using thermostable enzymes, like those of *Rasamsonia*, cost reduction can be achieved, because (i) less cooling of the pretreated material is required since higher temperatures are allowed during hydrolysis, and (ii) less water is added, which increases the dry matter content during hydrolysis and fermentation and thus increases the ethanol production capacity (amount produced per time unit per volume) of an ethanol plant. By using thermostable enzymes, like those of *Rasamsonia*, cost reduction may also be achieved by using cooling water having a higher temperature than the water that is used in a process with non-thermostable enzyme.

At the end of the hydrolysis, enzyme activities appear to be low, since little reducing sugars are released once almost all cellulose is converted. The amount of enzymatic activity present, however, has decreased only a little, assumingly mainly due to absorption of the enzymes to the substrate. By applying solid-liquid separation after hydrolysis, such as centrifugation, filtration, decantation, sedimentation, 60% or more (e.g. 70%) of the enzyme activity in solution can be recovered and re-used for hydrolysis of a new pretreated lignocellulosic material during the next hydrolysis.

Moreover, after solid/liquid separation the enzyme in solution can be separated from the solution containing reducing sugars and other hydrolysis products from the enzymatic actions. This separation can be done by techniques including, but not limited to, ultra- and microfiltration, centrifugation, decantation, sedimentation, with or without first adsorption of the enzyme to a carrier of any kind. For example, after hydrolysis of pretreated material with 0.175 ml/g material dry matter enzyme load for 20 h, 50% of the theoretical maximum amount of reducing sugars is liberated and after the same hydrolysis for 72 h, 90% of the theoretical maximum amount of reducing sugars is liberated. By centrifugation and ultrafiltration, 60-70% of the enzyme activity was recovered in the retentate, while the filtrate contained more than 80% of the liberated reducing sugars. By re-using the retentate, either as it is or after further purification and/or concentration, enzyme dosage during the next hydrolysis step can be reduced with 60 to 70%. The cost reduction achieved by using stable cellulolytic enzymes, such as those of Rasamsonia, in this way is the consequence of a lower enzyme dosage.

The process including enzyme recycling after hydrolysis, as described above, can be combined with recycling of the microorganism producing the fermentation product after fermentation and with the use of the reducing sugars containing filtrate as a substrate (purified and/or concentrated or diluted) in the propagation and cultivation of the microorganism producing the fermentation product and the microorganism producing the enzymes for hydrolysis. The reducing sugars containing filtrate can also be used as a substrate (purified and/or concentrated or diluted) in the production of the fermentation product by the fermentation product producing microorganism and the production of the enzymes for hydrolysis by the enzyme producing microorganism.

The thermostability of enzymes, like those from Rasamsonia, causes remaining cellulolytic activity after hydrolysis, fermentation and vacuum distillation in the thin stillage. The total activity of the enzyme is reduced during the three successive process steps. The thin stillage obtained after vacuum distillation can thus be re-used as a source of enzyme for a newly started hydrolysis-fermentation-distillation process cycle of pretreated material conversion into for example ethanol. The thin stillage can be used either in concentrated or (un)diluted form and/or purified and with or without additional enzyme supplementation.

In an optimal process, an amount of enzyme is supplemented into the thin stillage, before its re-use in a new process cycle, equal to the amount of activity lost during the three successive process steps of the previous process cycle. In this way over dosage of enzyme is avoided and thus most efficient use of enzyme is obtained. Moreover, by providing high enzyme dosage in the first process cycle, and supplementing enzyme equal to the amount of activity lost during the three successive process steps in the following process cycles, highest possible hydrolysis rates can be obtained in each process cycle resulting in short hydrolysis times of less than 48 h in combination with most efficient use of enzymes.

By applying mixing during hydrolysis, the chance of success of an effective enzyme-substrate binding is increased, which results in a more efficient use of the catalytic activity. This will result in a lower enzyme dosages and thus in lower costs, unless the mixing has a negative effect on the enzymes. Stable enzymes, like the thermostable enzymes from *Rasamsonia*, are robust and can resist circumstances of (locally) high shear and temperatures, which is the case during intensive mixing of slurries. The use of them in mixed systems is therefore beneficial and will lead to dosage and thus costs reduction.

Preferably, the enzyme compositions used in the enzymatic hydrolysis are stable. "Stable enzyme compositions" as used herein in relation to hydrolysis processes means that the enzyme compositions retain activity after 30 hours of hydrolysis reaction time, preferably at least 10%, 20%, 30%, 40%, 50%, 60%, 65%, 70%, 75%, 80% 85%, 90%, 95%, 96%, 97%, 98%, 99% or 100% of its initial activity after 30 hours of hydrolysis reaction time. Preferably, the enzyme composition retains activity after 40, 50, 60, 70, 80, 90 100, 150, 200, 250, 300, 350, 400, 450, 500 hours of hydrolysis reaction time.

Enzymes are present in the liquefaction step and in the saccharification step of the enzymatic hydrolysis. These enzymes may be the same or may be different. Furthermore, as described above, additional enzymes may be added during the liquefaction step and the saccharification step. The enzymes added may be enzymes that are already present in the liquefaction step and in the saccharification step. Alternatively, they may be different enzymes. Moreover, the additional enzymes added during the liquefaction step may differ or may be the same as the additional enzymes added during the saccharification step.

Lignocellulosic material as used herein includes any lignocellulosic and/or hemicellulosic material. Lignocellulosic material suitable for use in the processes as described herein includes biomass, e.g. virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane, cane straw, sugar cane bagasse, switch grass, miscanthus, energy cane, corn, corn stover, corn husks, corn cobs, canola stems, soybean stems, sweet sorghum, distillers dried grains, corn kernel including fiber from kernels, products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforementioned singularly or in any combination or mixture thereof.

In an embodiment the lignocellulosic material is pretreated before and/or during the enzymatic hydrolysis. Pretreatment methods are known in the art and include, but are not limited to, heat, mechanical, chemical modification, biological modification and any combination thereof. Pretreatment is typically performed in order to enhance the accessibility of the lignocellulosic material to enzymatic hydrolysis and/or hydrolyse the hemicellulose and/or solubilize the hemicellulose and/or cellulose and/or lignin, in the lignocellulosic material. In an embodiment, the pretreatment comprises treating the lignocellulosic material with steam explosion, hot water treatment or treatment with dilute acid or dilute base. Examples of pretreatment methods include, but are not limited to, steam treatment (e.g. treatment at 100-260° C., at a pressure of 7-45 bar, at neutral pH, for 1-10 minutes), dilute acid treatment (e.g. treatment with 0.1-5% $H_2SO_4$ and/or $SO_2$ and/or $HNO_3$ and/or HCl, in presence or absence of steam, at 120-200° C., at a pressure of 2-15 bar, at acidic pH, for 2-30 minutes), organosolv treatment (e.g. treatment with 1-1.5% $H_2SO_4$ in presence of organic solvent and steam, at 160-200° C., at a pressure of 7-30 bar, at acidic pH, for 30-60 minutes), lime treatment (e.g. treatment with 0.1-2% $NaOH/Ca(OH)_2$ in the presence of water/steam at 60-160° C., at a pressure of 1-10 bar, at alkaline pH, for 60-4800 minutes), ARP treatment (e.g. treatment with 5-15% $NH_3$, at 150-180° C., at a pressure of 9-17 bar, at alkaline pH, for 10-90 minutes), AFEX treatment (e.g. treatment with >15% $NH_3$, at 60-140° C., at a pressure of 8-20 bar, at alkaline pH, for 5-30 minutes).

The lignocellulosic material may be washed. In an embodiment the lignocellulosic material may be washed after the pretreatment. The washing step may be used to remove water soluble compounds that may act as inhibitors for the fermentation and/or hydrolysis step. The washing step may be conducted in manner known to the skilled person. Next to washing, other detoxification methods do exist. The lignocellulosic material may also be detoxified by any (or any combination) of these methods which include, but are not limited to, solid/liquid separation, vacuum evaporation, extraction, adsorption, neutralization, overliming, addition of reducing agents, addition of detoxifying enzymes such as laccases or peroxidases, addition of microorganisms capable of detoxification of hydrolysates.

In an embodiment the enzymatically hydrolysed lignocellulosic material is washed and/or detoxified. In an embodiment the solid fraction and/or the liquid fraction obtained after solid/liquid separation of the enzymatically hydrolysed lignocellulosic material is washed and/or detoxified. In an embodiment the liquid fraction obtained after solid/liquid separation of the enzymatically hydrolysed lignocellulosic material is subjected to a detoxification step and/or a concentration step. The detoxification step can be done by any of the methods as described above. The concentration step can be done by methods well known to a person skilled in the art including, but not limited to, centrifugation.

The enzyme composition can extremely effectively hydrolyze lignocellulosic material, for example corn stover, wheat straw, cane straw, and/or sugar cane bagasse, which can then be further converted into a product, such as ethanol, biogas, butanol, a plastic, an organic acid, a solvent, an animal feed supplement, a pharmaceutical, a vitamin, an amino acid, an enzyme or a chemical feedstock. Additionally, intermediate products from a process following the hydrolysis, for example lactic acid as intermediate in biogas production, can be used as building block for other materials.

In an embodiment the amount of enzyme composition added (herein also called enzyme dosage or enzyme load) in the hydrolysis is low. In an embodiment the amount of enzyme composition is 10 mg protein/g dry matter weight or lower, 9 mg protein/g dry matter weight or lower, 8 mg protein/g dry matter weight or lower, 7 mg protein/g dry matter weight or lower, 6 mg protein/g dry matter weight or lower, 5 mg protein/g dry matter or lower, 4 mg protein/g dry matter or lower, 3 mg protein/g dry matter or lower, 2 mg protein/g dry matter or lower, or 1 mg protein/g dry matter or lower (expressed as protein in mg protein/g dry matter). In an embodiment, the amount of enzyme composition is 5 mg enzyme/g dry matter weight or lower, 4 mg enzyme/g dry matter weight or lower, 3 mg enzyme/g dry matter weight or lower, 2 mg enzyme/g dry matter weight or lower, 1 mg enzyme/g dry matter weight or lower, 0.5 mg enzyme/g dry matter weight or lower, 0.4 mg enzyme composition/g dry matter weight or lower, 0.3 mg enzyme/g dry matter weight or lower, 0.25 mg enzyme/g dry matter weight or lower, 0.20 mg enzyme/g dry matter weight or lower, 0.18 mg enzyme/g dry matter weight or lower, 0.15 mg enzyme/g dry matter weight or lower or 0.10 mg enzyme/g dry matter weight or lower (expressed as total of cellulase enzymes in mg enzyme/g dry matter).

In an embodiment the enzyme composition is used in the enzymatic hydrolysis in an amount of 4.5 mg to 15 mg protein/gram dry matter weight of glucans in the lignocellulosic material. In an embodiment the enzyme composition is used in the enzymatic hydrolysis in an amount of 5 mg to 12 mg protein/gram dry matter weight of glucans in the lignocellulosic material. In an embodiment the enzyme composition is used in the enzymatic hydrolysis in an amount of 6 mg to 10 mg protein/gram dry matter weight of glucans in the lignocellulosic material.

The pH during the enzymatic hydrolysis may be chosen by the skilled person. In an embodiment the pH during the hydrolysis may be 3.0 to 6.5. The enzymes used may have a broad pH range of up to 2 pH units, up to 3 pH units, up to 5 pH units. The optimum pH may lie within the limits of pH 2.0 to 8.0, 2.5 to 7.5, 3.0 to 7.0, 3.5 to 6.5, 4.0 to 5.0, 4.0 to 4.5 or is about 4.2. The pH used in the liquefaction step of the enzymatic hydrolysis and the saccharification step of the enzymatic hydrolysis may differ or may be the same. In case different enzymes are used during the liquefaction step and the saccharification step, the optimum pH of said enzymes may differ or may be the same.

In an embodiment the hydrolysis step is conducted until 70% or more, 80% or more, 85% or more, 90% or more, 92% or more, 95% or more of available sugar in the lignocellulosic material is released.

Significantly, a hydrolysis process as described herein may be carried out using high levels of dry matter (of the lignocellulosic material) in the hydrolysis reaction. In an embodiment the dry matter content at the end of the enzymatic hydrolysis is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the enzymatic hydrolysis is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

In an embodiment the dry matter content at the end of the liquefaction step of the enzymatic hydrolysis is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the liquefaction step of the enzymatic hydrolysis is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

In an embodiment the dry matter content at the end of the saccharification step of the enzymatic hydrolysis is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the saccharification step of the enzymatic hydrolysis is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

As described above, the present disclosure also relates to a process for producing a fermentation product from a lignocellulosic material, which process comprises the steps of (a) hydrolysing the lignocellulosic material with an enzyme composition as described herein to obtain a sugar, (b) fermenting the obtained sugar by contacting the obtained sugar with a fermenting microorganism to produce the fermentation product, and (c) optionally, recovering the fermentation product.

In an embodiment the fermentation (i.e. step b) is performed in one or more containers. In an embodiment the fermentation is done by an alcohol producing microorganism to produce alcohol. In an embodiment the fermentation is done by an organic acid producing microorganism to produce an organic acid. The fermentation by an alcohol producing microorganism to produce alcohol can be done in the same container(s) wherein the enzymatic hydrolysis is performed. Alternatively, the fermentation by an alcohol producing microorganism to produce alcohol and the fermentation by an organic acid producing microorganism to produce an organic acid can be performed in one or more separate containers, but may also be done in one or more of the same containers.

In an embodiment the fermentation is done by a yeast. In an embodiment the alcohol producing microorganism and/or the organic acid producing microorganism is a yeast. In an embodiment the alcohol producing microorganism is able to ferment at least a C5 sugar and at least a C6 sugar. In an embodiment the organic acid producing microorganism is able to ferment at least a C6 sugar. In an embodiment the alcohol producing microorganism and the organic acid producing microorganism are different microorganisms. In another embodiment the alcohol producing microorganism and the organic acid producing microorganism are the same microorganism, i.e. the alcohol producing microorganism is also able to produce organic acid such as succinic acid.

In a further aspect, the present disclosure thus includes fermentation processes in which a microorganism is used for the fermentation of a carbon source comprising sugar(s), e.g. glucose, L-arabinose and/or xylose. The carbon source may include any carbohydrate oligo- or polymer comprising L-arabinose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case, the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation time may be shorter than in conventional fermentation at the same conditions, wherein part of the enzymatic hydrolysis still has to take part during fermentation. In one embodiment, the fermentation time is 100 hours or less, 90 hours or less, 80 hours or less, 70 hours or less, or 60 hours or less, for a sugar composition of 50 g/l glucose and corresponding other sugars from the lignocellulosic material (e.g. 50 g/l xylose, 35 g/l L-arabinose and 10 g/l galactose). For more dilute sugar compositions, the fermentation time may correspondingly be reduced. In an embodiment the fermentation time of the ethanol production step is between 10 and 50 hours for ethanol made out of C6 sugars and between 20 and 100 hours for ethanol made out of C5 sugars. In an embodiment the fermentation time of the succinic acid production step is between 20 and 70 hours.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating NAD+. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotics and a cephalosporin. In a preferred embodiment, the fermentation process is anaerobic. An anaerobic process is advantageous, since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

In an embodiment the alcohol fermentation process is anaerobic, while the organic acid fermentation process is aerobic, but done under oxygen-limited conditions.

The fermentation process is preferably run at a temperature that is optimal for the microorganism used. Thus, for most yeasts or fungal cells, the fermentation process is performed at a temperature which is less than 42° C., preferably 38° C. or lower. For yeast or filamentous fungal host cells, the fermentation process is preferably performed at a temperature which is lower than 35, 33, 30 or 28° C. and at a temperature which is higher than 20, 22, or 25° C. In an embodiment the alcohol fermentation step and the organic acid fermentation step are performed between 25° C. and 35° C.

In an embodiment, the fermentations are conducted with a fermenting microorganism. In an embodiment, the alcohol (e.g. ethanol) fermentations of C5 sugars are conducted with a C5 fermenting microorganism. In an embodiment, the alcohol (e.g. ethanol) fermentations of C6 sugars are conducted with a C5 fermenting microorganism or a commercial C6 fermenting microorganism. Commercially available yeast suitable for ethanol production include, but are not limited to, BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Food Specialties), GERT STRAND™ (Gert Strand AB, Sweden), and SUPERSTART™ and THERMOSACC™ fresh yeast (Ethanol Technology, WI, USA).

In an embodiment propagation of the alcohol producing microorganism and/or the organic acid producing microorganism is performed in one or more propagation containers. After propagation, the alcohol producing microorganism and/or the organic acid producing microorganism may be added to one or more fermentation containers. Alternatively, the propagation of the alcohol producing microorganism and/or the organic acid producing microorganism is combined with the fermentation by the alcohol producing microorganism and/or the organic acid producing microorganism to produce alcohol and/or organic acid, respectively.

In an embodiment the alcohol producing microorganism is a microorganism that is able to ferment at least one C5 sugar. Preferably, it also is able to ferment at least one C6 sugar. In an embodiment the present disclosure also describes a process for the preparation of ethanol from lignocellulosic material, comprising the steps of (a) performing a process for the preparation of a sugar product from lignocellulosic material as described herein, (b) fermentation of the enzymatically hydrolysed lignocellulosic material to produce ethanol; and (c) optionally, recovery of the ethanol. The fermentation can be done with a microorganism that is able to ferment at least one C5 sugar.

In an embodiment the organic acid producing microorganism is a microorganism that is able to ferment at least one C6 sugar. In an embodiment the present disclosure decribes a process for the preparation of succinic acid from lignocellulosic material, comprising the steps of (a) performing a process for the preparation of a sugar product from lignocellulosic material as described herein, (b) fermentation of the enzymatically hydrolysed lignocellulosic material to produce succinic acid; and (c) optionally, recovery of the succinic acid. The fermentation can be done with a microorganism that is able to ferment at least one C6 sugar.

The alcohol producing microorganisms may be a prokaryotic or eukaryotic organism. The microorganism used in the process may be a genetically engineered microorganism. Examples of suitable alcohol producing organisms are yeasts, for instance *Saccharomyces*, e.g. *Saccharomyces cerevisiae*, *Saccharomyces pastorianus* or *Saccharomyces uvarum*, *Hansenula*, *Issatchenkia*, e.g. *Issatchenkia orientalis*, *Pichia*, e.g. *Pichia stipites* or *Pichia pastoris*, *Kluyveromyces*, e.g. *Kluyveromyces fagilis*, *Candida*, e.g. *Candida pseudotropicalis* or *Candida acidothermophilum*, *Pachysolen*, e.g. *Pachysolen tannophilus* or bacteria, for instance *Lactobacillus*, e.g. *Lactobacillus lactis*, *Geobacillus*, *Zymomonas*, e.g. *Zymomonas mobilis*, *Clostridium*, e.g. *Clostridium phytofermentans*, *Escherichia*, e.g. *E. coli*, *Klebsiella*, e.g. *Klebsiella oxytoca*. In an embodiment the microorganism that is able to ferment at least one C5 sugar is a yeast. In an embodiment, the yeast belongs to the genus *Saccharomyces*, preferably of the species *Saccharomyces cerevisiae*. The yeast, e.g. *Saccharomyces cerevisiae*, used in the processes as described herein is capable of converting hexose (C6) sugars and pentose (C5) sugars. The yeast, e.g. *Saccharomyces cerevisiae*, used in the processes as described herein can anaerobically ferment at least one C6 sugar and at least one C5 sugar. For example, the yeast is capable of using L-arabinose and xylose in addition to glucose anaerobically. In an embodiment, the yeast is capable of converting L-arabinose into L-ribulose and/or xylulose 5-phosphate and/or into a desired fermentation product, for example into ethanol. Organisms, for example *Saccharomyces cerevisiae* strains, able to produce ethanol from L-arabinose may be produced by modifying a host yeast introducing the araA (L-arabinose isomerase), araB (L-ribuloglyoxalate) and araD (L-ribulose-5-P4-epimerase) genes from a suitable source. Such genes may be introduced into a host cell in order that it is capable of using arabinose. Such an approach is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens*, and/or *Gramella forsetii*, as disclosed in WO 2009011591. In an embodiment, the yeast may also comprise one or more copies of xylose isomerase gene and/or one or more copies of xylose reductase and/or xylitol dehydrogenase.

The yeast may comprise one or more genetic modifications to allow the yeast to ferment xylose. Examples of genetic modifications are introduction of one or more xylA-gene, XYL1 gene and XYL2 gene and/or XKS1-gene; deletion of the aldose reductase (GRE3) gene; overexpression of PPP-genes TAL1, TKL1, RPE1 and RKI1 to allow the increase of the flux through the pentose phosphate pathway in the cell. Examples of genetically engineered yeast are described in EP1468093 and/or WO2006/009434.

An example of a suitable commercial yeast is RN1016 that is a xylose and glucose fermenting *Saccharomyces cerevisiae* strain from DSM, the Netherlands.

In an embodiment, the fermentation process for the production of ethanol is anaerobic. Anaerobic has already been defined earlier herein. In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

Alternatively to the fermentation processes described above, at least two distinct cells may be used, this means this process is a co-fermentation process. All preferred embodiments of the fermentation processes as described above are also preferred embodiments of this co-fermentation process: identity of the fermentation product, identity of source of L-arabinose and source of xylose, conditions of fermentation (aerobic or anaerobic conditions, oxygen-limited conditions, temperature at which the process is being carried out, productivity of ethanol, yield of ethanol).

The organic acid producing microorganisms may be a prokaryotic or eukaryotic organism. The microorganism used in the process may be a genetically engineered microorganism. Examples of suitable organic acid producing organisms are yeasts, for instance *Saccharomyces*, e.g. *Saccharomyces cerevisiae*; fungi for instance *Aspergillus* strains, such as *Aspergillus niger* and *Aspergillus fumigatus*, *Byssochlamys nivea*, *Lentinus degener*, *Paecilomyces varioti* and *Penicillium viniferum*; and bacteria, for instance *Anaerobiospirillum succiniciproducens*, *Actinobacillus succinogenes*, *Mannhei succiniciproducers* MBEL 55E, *Escherichia coli*, *Propionibacterium* species, *Pectinatus* sp., *Bacteroides* sp., such as *Bacteroides amylophilus*, *Ruminococcus flavefaciens*, *Prevotella ruminicola*, *Succcinimonas amylolytica*, *Succinivibrio dextrinisolvens*, *Wolinella succinogenes*, and *Cytophaga succinicans*. In an embodiment the organic acid producing microorganism that is able to ferment at least one C6 sugar is a yeast. In an embodiment, the yeast belongs to the genus *Saccharomyces*, preferably of the species *Saccharomyces cerevisiae*. The yeast, e.g. *Saccharomyces cerevisiae*, used in the production processes of organic acid as described herein is capable of converting hexose (C6) sugars. The yeast, e.g. *Saccharomyces cerevisiae*, used in the processes as described herein can anaerobically ferment at least one C6 sugar.

The overall reaction time (or the reaction time of hydrolysis step and fermentation step together) may be reduced. In one embodiment, the overall reaction time is 300 hours or less, 200 hours or less, 150 hours or less, 140 hours or less, 130 or less, 120 hours or less, 110 hours or less, 100 hours of less, 90 hours or less, 80 hours or less, 75 hours or less, or about 72 hours at 90% glucose yield. Correspondingly, lower overall reaction times may be reached at lower glucose yield.

Fermentation products that may be produced by the processes as described herein can be any substance derived from fermentation. They include, but are not limited to, alcohol (such as arabinitol, butanol, ethanol, glycerol, methanol, 1,3-propanediol, sorbitol, and xylitol); organic acid (such as acetic acid, acetonic acid, adipic acid, ascorbic acid, acrylic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, maleic acid, malic acid, malonic acid, oxalic acid, oxaloacetic acid, propionic acid, succinic acid, and xylonic acid); ketones (such as acetone); amino acids (such as aspartic acid, glutamic acid, glycine, lysine, serine, tryptophan, and threonine); alkanes (such as pentane, hexane, heptane, octane, nonane, decane, undecane, and dodecane), cycloalkanes (such as cyclopentane, cyclohexane, cycloheptane, and cyclooctane), alkenes (such as pentene, hexene, heptene, and octene); and gases (such as methane, hydrogen ($H_2$), carbon dioxide ($CO_2$), and carbon monoxide (CO)). The fermentation product can also be a protein, a vitamin, a pharmaceutical, an animal feed supplement, a specialty chemical, a chemical feedstock, a plastic, a solvent, ethylene, an enzyme, such as a protease, a cellulase, an amylase, a glucanase, a lactase, a lipase, a lyase, an oxidoreductase, a transferase or a xylanase. In a preferred embodiment an organic acid and/or an alcohol is prepared in the fermentation processes as described herein. In a preferred embodiment succinic acid and/or ethanol is prepared in the fermentation processes as described herein.

The beneficial effects as described herein are found for several lignocellulosic materials and therefore believed to be present for the hydrolysis of all kind of lignocellulosic materials. The beneficial effects are found for several enzymes and therefore believed to be present for all kind of hydrolysing enzyme compositions.

EXAMPLES

Example 1

Preparation of enzyme blends with different $R_{EG}$ and $R_{LPMO}$

A single endoglucanase (EG) (see WO 01/70998) and a single lytic polysaccharide monooxygenase (LPMO) (see WO 2012/000892) were produced using *A. niger* as expression host according to the method as described in WO 2014/202622. Additionally, a cellulase composition was produced according to the method as described in Example 3 of WO 2011/000949.

The protein concentration of the endoglucanase, lytic polysaccharide monooxygenase and the cellulase composition was determined using the following TCA-aceton precipitation-biuret assay. Protein samples were diluted with water to a concentration between 2 and 8 mg/ml. Bovine serum albumin (BSA) dilutions (0, 1, 2, 5, 8 and 10 mg/ml) were made and included as samples to generate a calibration curve. Of each diluted protein sample, 270 µl was transferred into a 10 ml tube containing 830 µl of a 12% (w/v) trichloro acetic acid solution in acetone and mixed thoroughly. Subsequently, the tubes were incubated on ice water for one hour and centrifuged for 30 minutes at 4° C. and 4000×g. The supernatant was discarded and pellets were dried by inverting the tubes on a tissue and letting them stand for 30 minutes at room temperature. Next, 3 ml BioQuant Biuret reagent mix was added to the pellet in the tube and the pellet was solubilized upon mixing followed by addition of 1 ml water. The tube was mixed thoroughly and incubated at room temperature for 30 minutes. The absorption of the mixture was measured at 546 nm with a water sample used as a blank measurement and the protein concentration was calculated via the BSA calibration line.

Next, different enzyme blends were prepared. The enzyme blends that were prepared and their make-up are listed in Table 1. The percentages indicate the relative amount of each component (cellulase composition, endoglucanase and/or lytic polysaccharide monooxygenase) of the total protein dosed in a hydrolysis assay (see Example 2). For example, in case of a total enzyme dosage of 2.5 mg protein per gram of dry matter in a hydrolysis assay, the cellulase composition was dosed at 100% for blend 0, and thus at 2.5 mg/g dry matter. In blend 1, 95% of the total protein was dosed as cellulase composition (i.e. 2.375 mg/g dry matter) and 5% of total protein was dosed as endoglucanase (i.e. 0.125 mg/g dry matter) and so on.

In Table 2, the total amount of endoglucanase, lytic polysaccharide monooxygenase, beta-xylosidase and endoxylanase in the final blend are given. The total amount is a calculated value using the protein concentrations of the single endoglucanase and lytic polysaccharide monooxygenase (produced in *A. niger*) and the endoglucanase, lytic polysaccharide monooxygenase, beta-xylosidase and endoxylanase content in the cellulase composition as determined using proteomics as described in Example 14 of WO 2011/000949.

Example 2

Hydrolysis performance of enzyme blends with different $R_{EG}$ and $R_{LPMO}$

The hydrolysis activity of the enzyme blends was determined in a hydrolysis assay. The total amount of protein dosed in each hydrolysis experiment was kept constant at 2.5 mg/g dry matter.

For the preparation of low acid pretreated corn stover, a pilot scale pretreatment reactor was used operating at steady state conditions of 186° C., 6.7 minutes residence time. Prior to the heat treatment, the corn stover was impregnated with $H_2SO_4$ for 10 minutes to set the pH at 2.5 (determined at room temperature after the pretreatment).

In the hydrolysis assay, the blends were added to the low acid pretreated corn stover, incubated for 72 hours at pH 4.5 at a temperature of 62° C. and the hydrolysis activity of the blends was compared via their ability to release glucose and xylose from the corn stover feedstock. In the assay, the concentration of the lignocellulosic material was set to 15% (w/w) dry matter and the total cellulase concentration was 2.5 mg protein per gram of dry matter. The 15% dry matter suspension was prepared via dilution of a more concentrated suspension with water and subsequent adjustment of the pH of the obtained slurry to pH 4.5 with a 4 M NaOH solution. The hydrolysis reactions were performed in a total volume of 20 g in 40 ml centrifuge bottles (Nalgene Oakridge). Incubation was done in an oven incubator at 62° C. (Techne HB-1 D hybridization oven), while rotating at set-point 3. After incubation for 72 hours at pH 4.5 and a temperature of 62° C., hydrolysate samples were centrifuged and the glucose and xylose content of the supernatant was analyzed using a High-Performance Liquid Chromatography System (Agilent 1100) equipped with a refection index detector (Agilent 1260 Infinity). The separation of the sugars was done by using a 300×7.8 mm Aminex HPX-87P (Bio rad cat no 125-0098) column; Pre-column: Micro guard Carbo-P (Bio Rad cat no 125-0119); mobile phase was HPLC grade water; flow rate of 0.6 ml/min and a column temperature of 85° C. The injection volume was 10 µl. The samples were diluted with HPLC grade water to a maximum of 2.5 g/l glucose and filtered by using 0.2 µm filter (Afridisc LC25 mm syringe filter PVDF membrane). The glucose and xylose were identified and quantified according to the retention time, which was compared to the external glucose standard (D-(+)-Glucose, Sigma cat no: G7528) ranging from 0.2; 0.4; 1.0; 2.0 g/l and xylose standard (xylose, Sigma) ranging from 0.2; 0.4; 1.0; 2.0 g/l).

Subsequently, the concentration glucose and xylose released from the lignocellulosic material by the different enzyme blends was used to compare the hydrolysis performance of the blends. The glucose and xylose released by the cellulase composition was used as a reference and the performance of all other blends was calculated relative to the cellulase composition using the following formula:

Performance blend=(Total glucose (g/l)+xylose (g/l) released by blend)/(total glucose (g/l)+xylose (g/l) released by cellulase composition)*100%

For the cellulase composition (blend 0) as well as the enzyme blends with single endoglucanase addition and/or single lytic polysaccharide monooxygenase addition, three ratios were calculated.

The ratio endoglucanase ($R_{EG}$), which is defined as the total weight of endoglucanases in the mix divided by the total weight of endoglucanases and the total weight of lytic polysaccharide monooxygenases in the mix, can be calculated by the formula: $R_{EG}$=total EG/(total EG+total LPMO).

The ratio lytic polysaccharide monooxygenases ($R_{LPMO}$), which is defined as the total weight of lytic polysaccharide monooxygenases in the mix divided by the total weight of lytic polysaccharide monooxygenases and the total weight of endoglucanases in the mix can be calculated by the formula: $R_{LPMO}$=total LPMO/(total EG+total LPMO).

The ratio hemicellulase ($R_{HC}$), which is defined as the total weight of beta-xylosidases and endoxylanases in the enzyme composition divided by the total weight of beta-xylosidases, endoxylanases and lytic polysaccharide monooxygenases in the enzyme composition, can be calculated by the formula: $R_{HC}$=(total BX+total EX)/(total BX+total EX+total LPMO).

The hydrolysis performance of the various enzyme blends are shown in Table 3. The data clearly show that blends having a similar $R_{EG}$ and $R_{LPMO}$ as enzyme blends described in WO 2011/000949 (the blends in WO 2011/000949 have a $R_{EG}$ of 0.35-0.62 and a $R_{LPMO}$ of 0.38-0.65) have a lower hydrolysis performance than enzyme blends of the present disclosure that have a $R_{EG}$ from 0.05-0.34 and a $R_{LPMO}$ from 0.66-0.95.

The tested enzyme blends that have a $R_{EG}$ outside the range of 0.05-0.34, a $R_{LPMO}$ outside the range of 0.66-0.95 and a $R_{HC}$ outside the range of 0.15-0.65, i.e. enzyme blends 0, 1, 2 and 7, have a hydrolysis performance of 100% or lower, while the enzyme blends that have a $R_{EG}$ of 0.05-0.34, a $R_{LPMO}$ of 0.66-0.95 and a $R_{HC}$ of 0.15-0.65, i.e. enzyme blends 3, 4, 5 and 6, have a hydrolysis performance that is higher than 100%. Such blends thus have an improved performance.

TABLE 1

Cellulase blends.

| Blend | Cellulase composition (% w/w)* | Single EG (*A. niger* produced) (% w/w)* | Single LPMO (*A. niger* produced) (% w/w)* |
|---|---|---|---|
| 0 | 100 | 0 | 0 |
| 1 | 95 | 5 | 0 |
| 2 | 97.5 | 2.5 | 0 |
| 3 | 95 | 0 | 5 |
| 4 | 90 | 0 | 10 |
| 5 | 80 | 0 | 20 |
| 6 | 70 | 0 | 30 |
| 7 | 40 | 0 | 60 |

*The indicated percentages are weight percentages of the cellulase composition, the EG and/or the LPMO versus the total protein in the final blend.

TABLE 2

Cellulase blends.

| Blend | Total EG in final blend (EG content in cellulose composition + single EG (*A. niger* produced) (% w/w) | Total LPMO in final blend (LPMO content in cellulase composition + single LPMO (*A. niger* produced) (% w/w) | Total BX in final blend (BX content in cellulase composition (% w/w) | Total EX in final blend (EX content in cellulase composition (% w/w) |
|---|---|---|---|---|
| 0 | 4.4 | 5.9 | 4.7 | 9.2 |
| 1 | 9.2 | 5.6 | 4.4 | 8.7 |
| 2 | 6.8 | 5.8 | 4.5 | 9.0 |
| 3 | 4.2 | 10.6 | 4.4 | 8.7 |
| 4 | 4.0 | 15.3 | 4.2 | 8.3 |
| 5 | 3.6 | 24.8 | 3.7 | 7.4 |
| 6 | 3.1 | 34.2 | 3.3 | 6.4 |
| 7 | 1.8 | 62.4 | 1.9 | 3.7 |

TABLE 3

Hydrolysis performance of enzyme blends and values for $R_{EG}$, $R_{LPMO}$ and $R_{HC}$.

| Blend | $R_{EG}$ | $R_{LPMO}$ | $R_{HC}$ | Hydrolysis performance |
|---|---|---|---|---|
| 1 | 0.62 | 0.38 | 0.7 | 97.7% |
| 2 | 0.54 | 0.46 | 0.7 | 96.3% |
| 0 | 0.43 | 0.57 | 0.7 | 100% |
| 3 | 0.28 | 0.72 | 0.55 | 101.6% |
| 4 | 0.21 | 0.79 | 0.45 | 102.2% |
| 5 | 0.13 | 0.87 | 0.31 | 105.6% |
| 6 | 0.08 | 0.92 | 0.22 | 103.2% |
| 7 | 0.03 | 0.97 | 0.08 | 97.1% |

The invention claimed is:
1. An enzyme composition comprising an endoglucanase, a lytic polysaccharide monooxygenase and a hemicellulase, wherein the hemicellulase comprises a beta-xylosidase (BX) and/or an endoxylanase (EX), and wherein:

the endoglucanase (EG) is present according to the following formula with a ratio ($R_{EG}$) from 0.08 to 0.28:

$$R_{EG} = \frac{\text{total EG weight}}{\text{(total EG weight)} + \text{(total LPMO weight)}};$$

the lytic polysaccharide monooxygenase (LPMO) is present according to the following formula with a ratio ($R_{LPMO}$) from 0.72 to 0.92:

$$R_{LPMO} = \frac{\text{total LPMO weight}}{\text{(total LPMO weight)} + \text{(total EG weight)}}; \text{ and}$$

the hemicellulase (HC) is present according to the following formula with a ratio ($R_{HC}$) from 0.22 to 0.55:

$$R_{HC} = \frac{\text{(total BX weight)} + \text{(total EX weight)}}{\text{(total BX weight)} + \text{(total EX weight)} + \text{(total LPMO weight)}}.$$

2. The enzyme composition according to claim 1, wherein the endoglucanase comprises a GH5 endoglucanase and/or a GH7 endoglucanase.

3. The enzyme composition according to claim 1, wherein the lytic polysaccharide monooxygenase comprises an AA9 lytic polysaccharide monooxygenase.

4. The enzyme composition according to claim 1, wherein the beta-xylosidase comprises a GH3 beta-xylosidase.

5. The enzyme composition according to claim 1, wherein the endoxylanase comprises a GH10 endoxylanase.

6. The enzyme composition according to claim 1, wherein the enzyme composition comprises endoglucanase in an amount of 3% to 5% (w/w) of the total amount of protein in the enzyme composition.

7. The enzyme composition according to claim 1, wherein the enzyme composition comprises lytic polysaccharide monoxygenase in an amount of 10% to 30% (w/w) of the total amount of protein in the enzyme composition.

8. The enzyme composition according to claim 1, further comprising a beta-glucosidase, a cellobiohydrolase I and a cellobiohydrolase II.

9. The enzyme composition according to claim 1, which is a whole fermentation broth.

10. A process for preparation of a sugar from lignocellulosic material comprising:
a) hydrolysing the lignocellulosic material with an enzyme composition according to claim 1 to obtain the sugar, and
b) optionally, recovering the sugar.

11. A process for producing a fermentation product from a lignocellulosic material, which process comprises:
a) hydrolysing the lignocellulosic material with an enzyme composition according to claim 1 to obtain a sugar,
b) fermenting obtained sugar by contacting the obtained sugar with a fermenting microorganism to produce the fermentation product, and
c) optionally, recovering the fermentation product.

12. The process according to claim 10, wherein the enzyme composition is used in an amount of 4.5 mg to 15 mg protein/gram dry matter weight of glucans in the lignocellulosic material.

13. The process according to claim 10, wherein the lignocellulosic material is subjected to pretreatment before the enzymatic hydrolysis.

14. The process according to claim 13, wherein the pretreatment is steam treatment, dilute acid treatment, organosolv treatment, lime treatment, ARP treatment or AFEX treatment.

15. The process according to claim 11, wherein the fermentation product is alcohol and the fermenting microorganism is an alcohol producing microorganism that is able to ferment at least one C5 sugar.

* * * * *